United States Patent
Nazarifar et al.

(10) Patent No.: US 6,824,525 B2
(45) Date of Patent: Nov. 30, 2004

(54) SURGICAL CASSETTE AND CONSUMABLES FOR COMBINED OPHTHALMIC SURGICAL PROCEDURE

(75) Inventors: Nader Nazarifar, Laguna Niguel, CA (US); Dennis L. Steppe, Corona, CA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 10/390,273

(22) Filed: Mar. 17, 2003

(65) Prior Publication Data

US 2003/0163138 A1 Aug. 28, 2003

Related U.S. Application Data

(63) Continuation of application No. 09/675,683, filed on Sep. 29, 2000, now Pat. No. 6,561,999.

(51) Int. Cl.[7] ............................. A61F 9/00; A61M 1/00
(52) U.S. Cl. ......................................... 604/30; 604/521
(58) Field of Search ............................ 604/27, 28, 30, 604/35, 43, 44, 45, 48, 151, 521

(56) References Cited

U.S. PATENT DOCUMENTS

| | | |
|---|---|---|
| 4,475,904 A | 10/1984 | Wang |
| 4,713,051 A | 12/1987 | Steppe et al. |
| 4,735,610 A | 4/1988 | Akkas et al. |
| 4,750,643 A | 6/1988 | Wortrich |
| 4,758,238 A | 7/1988 | Sundblom et al. |
| 4,813,927 A | 3/1989 | Morris et al. |
| 4,832,685 A | 5/1989 | Haines |
| 4,900,301 A | 2/1990 | Morris et al. |
| 4,935,005 A | 6/1990 | Haines |
| 4,963,131 A | 10/1990 | Wortrich |
| 5,032,111 A | 7/1991 | Morris et al. |
| 5,041,096 A | 8/1991 | Beuchat et al. |
| 5,047,009 A | 9/1991 | Morris et al. |
| 5,163,900 A | 11/1992 | Wortrich |
| 5,267,956 A | 12/1993 | Beuchat |
| 5,282,787 A | 2/1994 | Wortrich |
| D352,106 S | 11/1994 | Fanney et al. |
| 5,364,342 A | 11/1994 | Beuchat et al. |
| 5,499,969 A | 3/1996 | Beuchat et al. |
| D375,553 S | 11/1996 | Creed et al. |
| 5,582,601 A | 12/1996 | Wortrich et al. |
| 5,588,815 A | 12/1996 | Zaleski, II |
| D380,550 S | 7/1997 | Dennewill et al. |
| 5,676,530 A | 10/1997 | Nazarifar |
| 5,747,824 A | 5/1998 | Jung et al. |
| 5,800,396 A | 9/1998 | Fanney et al. |
| 5,897,524 A | 4/1999 | Wortrich et al. |
| 5,899,674 A | 5/1999 | Jung et al. |
| 6,059,544 A | 5/2000 | Jung et al. |

FOREIGN PATENT DOCUMENTS

| | | |
|---|---|---|
| CA | 1068572 | 12/1979 |
| CA | 1068574 | 12/1979 |
| DE | 38 22 011 A1 | 1/1990 |
| DE | 198 52 574 A1 | 5/2000 |
| EP | 0 776 670 A2 | 6/1997 |

*Primary Examiner*—Harry B. Tanner
(74) *Attorney, Agent, or Firm*—W. David Lee (57) ABSTRACT

A surgical cassette for use in a combined anterior segment and posterior segment ophthalmic surgical procedure is disclosed. The surgical cassette includes an irrigation inlet for receiving irrigation fluid from a source, a first irrigation outlet for providing irrigation fluid to a first ophthalmic microsurgical instrument, a first manifold fluidly coupling the irrigation inlet with the first irrigation outlet, a second irrigation outlet for providing irrigation fluid to a second ophthalmic microsurgical instrument, and a second manifold fluidly coupling the irrigation inlet with the second irrigation outlet. The surgical cassette greatly simplifies the combined procedure by eliminating the need for separate anterior segment and posterior segment cassettes for the combined procedure.

1 Claim, 5 Drawing Sheets

Fig. 8

SURGICAL CASSETTE AND CONSUMABLES FOR COMBINED OPHTHALMIC SURGICAL PROCEDURE

This application is a continuation of U.S. application Ser. No. 09/675,683, filed Sep. 29, 2000, now U.S. Pat. No. 6,561,999.

FIELD OF THE INVENTION

The present invention generally pertains to ophthalmic surgical procedures. More particularly, but not by way of limitation, the present invention pertains to combined anterior segment and posterior segment ophthalmic surgical procedures, as well as consumables utilized in such procedures.

DESCRIPTION OF THE RELATED ART

Ophthalmic surgical procedures are commonly classified as anterior segment surgical procedures, such as cataract surgery, and posterior segment procedures, such as vitreoretinal surgery. Traditionally, surgeons who performed anterior segment procedures did not typically perform posterior segment procedures, and vice versa. Therefore, two different sets of instrumentation and associated consumables were created for anterior segment surgery and posterior segment surgery. The Series 20000® Legacy® cataract surgical system, the Phaco-Emulsifier® aspirating unit, and their associated surgical cassettes, drainage bags, and tubing sets available from Alcon Laboratories, Inc. of Fort Worth, Tex. are examples of such anterior segment instrumentation and consumables. The Accurus® 400VS surgical system and its associated surgical cassettes, drainage bags, and tubing sets, are examples of such posterior segment instrumentation and consumables.

In posterior segment procedures involving phakic eyes, the crystalline lens may be surgically extracted. Such extraction is typically performed using posterior segment instrumentation (e.g. a vitrectomy probe) and consumables via a lensectomy. Due to the anatomical relationship of the lens to the scleratomies, a lensectomy requires the removal of the posterior lens capsule. The removal of the posterior lens capsule precludes the implantation of an intraocular lens (IOL) into the posterior chamber, the anatomically preferred location for IOL implantation. In addition, it is believed that the removal of the posterior lens capsule contributes to secondary complications such as cystoid macular edema.

Recently, a new procedure typically referred to as a combined anterior segment and posterior segment procedure, or "combined procedure", has been developed. A posterior segment surgeon typically performs the combined procedure. In an uncomplicated combined procedure, the posterior segment surgeon first performs an anterior segment procedure, such as a cataract removal via phacoemulsification with posterior chamber IOL implantation, using an anterior segment surgical system and its associated consumables. The surgeon then immediately performs a posterior segment procedure using a separate posterior segment surgical system and its associated consumables. In more complicated combined procedures, the posterior chamber IOL implantation is often deferred until completion of the posterior segment procedure.

Even more recently, surgical systems have been developed that support both an anterior segment procedure and a posterior segment procedure via a single surgical console. An example of such a system is the Accurus® 600DS surgical system available from Alcon Laboratories, Inc. Two groups of consumables (surgical cassette, drainage bag, tubing sets) are currently available for use with this surgical system.

Figure 1:
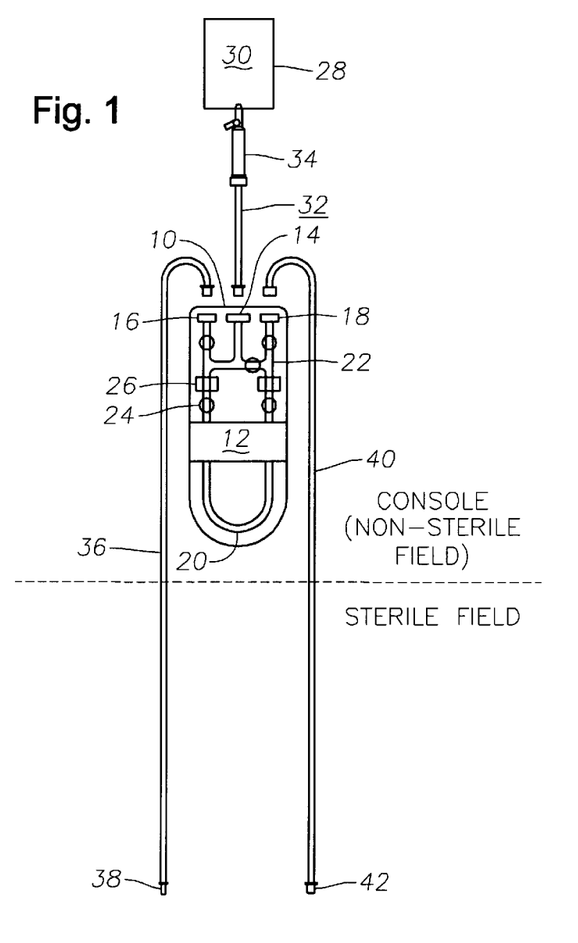
FIG. 1 is a schematic view of a conventional set of anterior segment consumables in their assembled form.

The first group of consumables is the Accurus® Anterior Pak available from Alcon Laboratories, Inc., which is for use only in anterior segment procedures. A schematic representation of the consumables in the Accurus® Anterior Pak, in their assembled form, is shown in FIG. 1. The Accurus® Anterior Pak includes a surgical cassette 10 having a vacuum chamber 12, an irrigation inlet 14, an irrigation outlet 16, and an aspiration port 18. As shown schematically in FIG. 1, a series of manifolds 22 fluidly couple vacuum chamber 12, irrigation inlet 14, irrigation outlet 16, and an aspiration port 18. Cassette 10 is disposed in a cassette receiving mechanism (not shown) in the Accurus® surgical system. As shown schematically in FIG. 1, the cassette receiving mechanism includes a series of occluder valves 24 and microreflux valves 26 for opening and closing various portions of manifolds 22. Cassette 10 further includes a pump manifold 20 that is used to drain aspirated fluid from vacuum chamber 12 into a drain bag (not shown) connected to cassette 10. A bottle 28 containing a conventional ophthalmic infusion fluid 30, such as saline solution or BSS PLUS® intraocular irrigating solution available from Alcon Laboratories, Inc., is disposed above cassette 10. Bottle 28 is not part of the Accurus® Anterior Pak. Bottle 28 is fluidly coupled to irrigation inlet 14 via tubing 32. A conventional drip chamber 34 may be fluidly coupled between bottle 28 and tubing 32. Tubing 36 is fluidly coupled to irrigation outlet 16. The distal end 38 of tubing 36 is for fluidly coupling to a conventional irrigation handpiece, the irrigation inlet of a conventional irrigation/aspiration handpiece, or the irrigation inlet of a conventional ultrasonic handpiece. Tubing 40 is fluidly coupled to aspiration port 18. The distal end 42 of tubing 40 is for fluidly coupling to the aspiration port of a conventional ultrasonic handpiece, or to the aspiration port of a conventional irrigation/aspiration handpiece. Tubing 32, 36, and 40 are preferably conventional medical grade flexible tubing.

Figure 2:
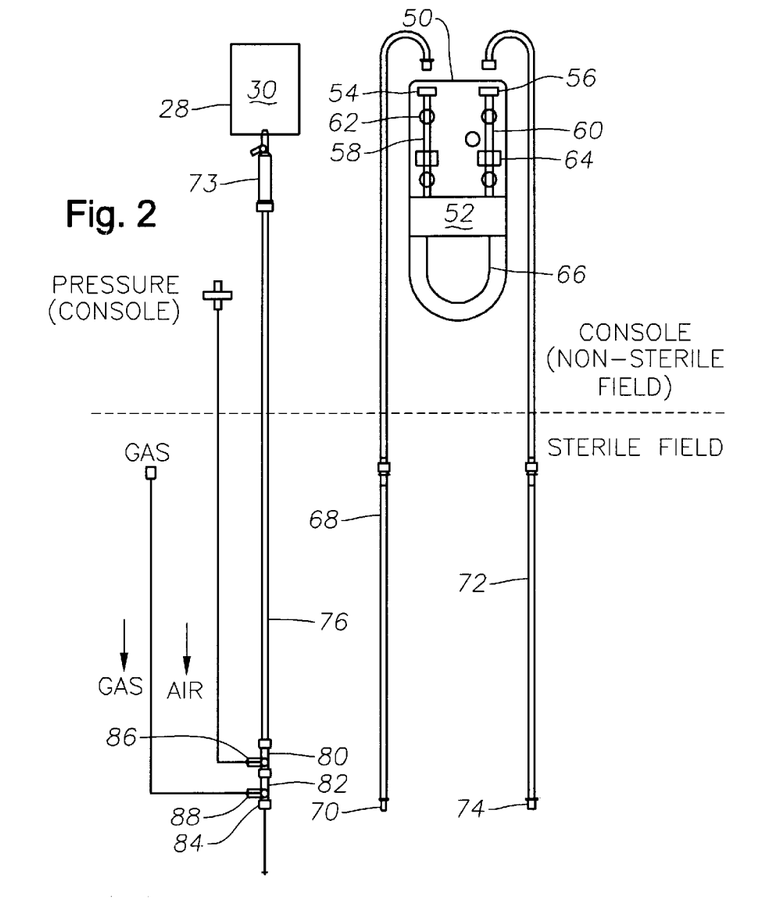
FIG. 2 is a schematic view of a conventional set of posterior segment consumbables in their assembled form.

The second group of consumables is the Total Plus™ Pak available from Alcon Laboratories, Inc., which is for use only in posterior segment procedures. A schematic representation of the consumables in the Total Plus™ Pak, in their assembled form, is shown in FIG. 2. The Total Plus™ Pak includes a surgical cassette 50 having a vacuum chamber 52, a first aspiration port 54, and a second aspiration port 56. As shown schematically in FIG. 2, a first manifold 58 fluidly couples vacuum chamber 52 and port 54, and a second manifold 60 fluidly couples vacuum chamber 52 and port 56. Cassette 50 is disposed in a cassette receiving mechanism (not shown) in the Accurus® surgical system. As shown schematically in FIG. 2, the cassette receiving mechanism includes a series of occluder valves 62 and microreflux valves 64 for opening and closing various portions of manifolds 58 and 60. Cassette 50 further includes a pump manifold 66 that is used to drain aspirated fluid from vacuum chamber 52 into a drain bag (not shown) connected to cassette 50. Tubing 68 is fluidly coupled to aspiration port 54. The distal end 70 of tubing 68 is for fluidly coupling to a conventional extrusion handpiece or a conventional ultrasonic handpiece used for pars plana lensectomy. Tubing 72 is fluidly coupled to aspiration port 56. The distal end 74 of tubing 72 is for fluidly coupling to the aspiration port of a conventional vitrectomy probe. A bottle 28 containing a conventional ophthalmic infusion fluid 30, such as saline solution or BSS PLUS® intraocular irrigating solution, is disposed above cassette 10. Bottle 28 is not part of the Total Plus™ Pak. Bottle 28 is fluidly coupled to tubing 76. A conventional drip chamber 78 may be fluidly coupled between bottle 30 and tubing 76. A stopcock 80 is fluidly coupled to tubing 76, and a stopcock 82 is fluidly coupled to stopcock 80. Stopcocks 80 and 82 are preferably conventional three-way stopcocks. An outlet 84 of stopcock 82 is for fluidly coupling to a conventional infusion cannula. An inlet 86 of stopcock 80 is for fluidly coupling to a source of pressurized air that can be used to perform a fluid/air exchange during a posterior segment procedure. An inlet 88 of stopcock 82 is for fluidly coupling to a source of pressurized gas, such a perfluorocarbon gas, that can be used to perform a fluid/gas exchange, or an air/gas exchange, during a posterior segment procedure. Tubing 68, 72, and 76 are preferably conventional medical grade flexible tubing.

Therefore, the Accurus® 600DS surgical system, and its associated consumables, greatly simplify the combined anterior segment and posterior segment ophthalmic surgical procedure. However, even with the Accurus® 600DS surgical system, a combined procedure requires the use of two separate sets of consumables. When changing from an anterior segment procedure to a posterior segment procedure, the surgeon and his or her staff must remove the anterior segment consumables and set up the surgical system with the posterior segment consumables. Therefore, a need continues to exist in the ophthalmic surgical field for ways to further simplify the combined anterior segment and posterior segment procedure for the surgeon.

SUMMARY OF THE INVENTION

The present invention is directed to a surgical cassette for use in a combined ophthalmic surgical procedure. The surgical cassette includes an irrigation inlet for receiving irrigation fluid from a source, a first irrigation outlet for providing irrigation fluid to a first ophthalmic microsurgical instrument, a first manifold fluidly coupling the irrigation inlet with the first irrigation outlet, a second irrigation outlet for providing irrigation fluid to a second ophthalmic microsurgical instrument, and a second manifold fluidly coupling the irrigation inlet with the second irrigation outlet. The surgical cassette greatly simplifies the combined procedure by eliminating the need for separate anterior segment and posterior segment cassettes for the combined procedure.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiment of the present invention and its advantages are best understood by referring to FIGS. 3 through 10 of the drawings, like numerals being used for like and corresponding parts of the various drawings.

FIGS. 3 through 8 illustrate a surgical cassette 100 according to a preferred embodiment of the present invention. Surgical cassette 100 is especially designed for use in a combined anterior segment and posterior segment ophthalmic surgical procedure, or "combined procedure". Cassette 100 is preferably formed from a body 102 and a mating cover 104 made of conventional plastics. Cover 104 preferably has a handle 106 for grasping cassette 100, and a header 107. Cassette 100 also generally includes a vacuum chamber 108, and irrigation inlet 110, an anterior irrigation outlet 112, a posterior irrigation outlet 114, a general aspiration port 116, a posterior aspiration port 118, a first vacuum chamber port 120, a second vacuum chamber port 122, a third vacuum chamber port 124, and a drainage bag port 126. The locations of anterior irrigation outlet 112 and posterior irrigation outlet 114 may be reversed, if desired. As shown best in FIG. 6, vacuum chamber port 120 preferably has an oval-shaped geometry that is capable of receiving two manifolds made from conventional medical grade flexible tubing.

Figure 3:
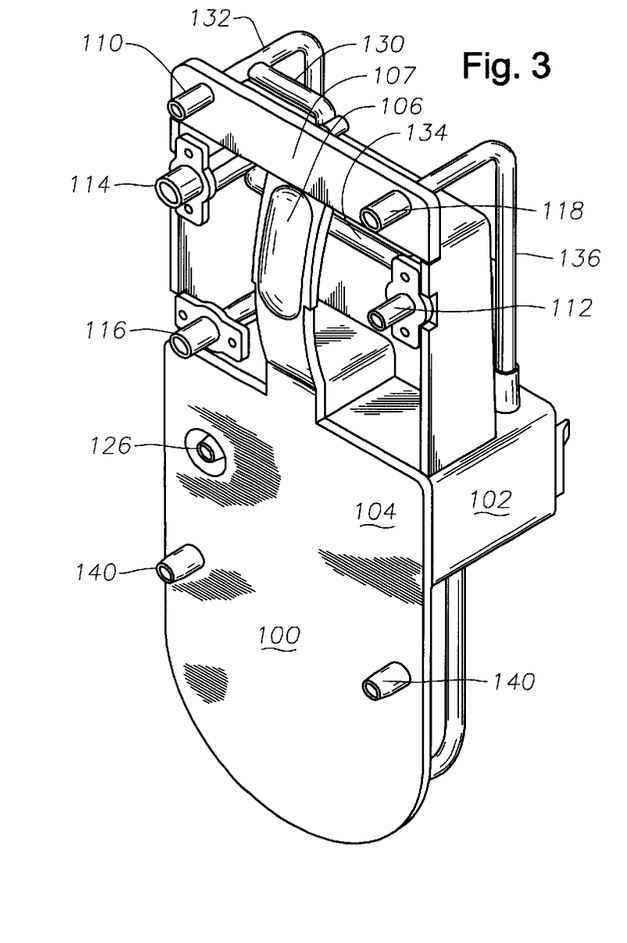
FIG. 3 is a front, perspective view of a surgical cassette for a combined ophthalmic surgical procedure according to a preferred embodiment of the present invention.
Figure 4:
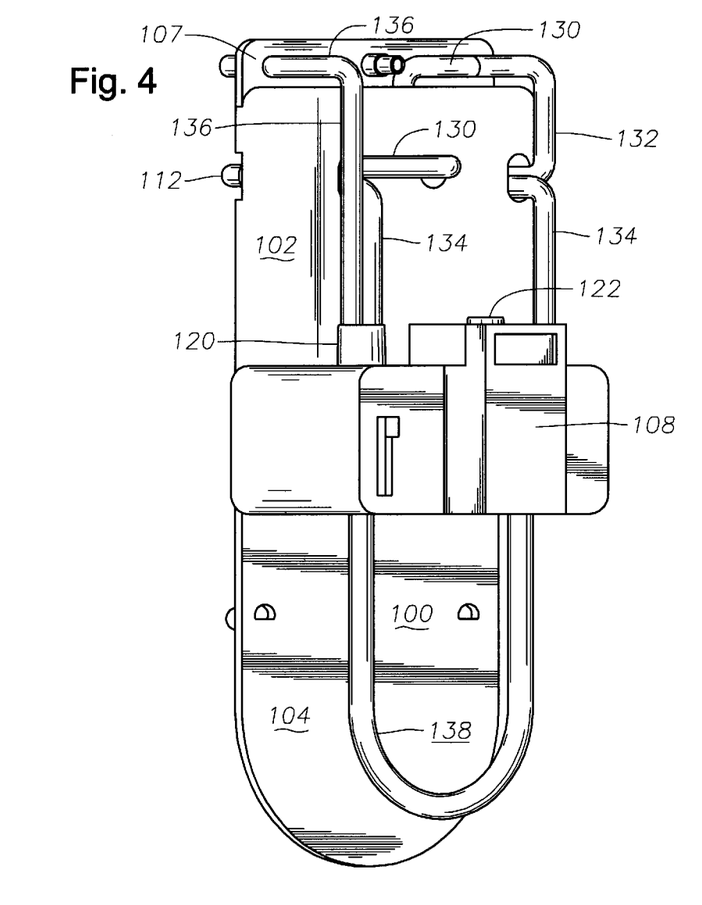
FIG. 4 is a rear, perspective view of the surgical cassette of FIG. 3.
Figure 5:
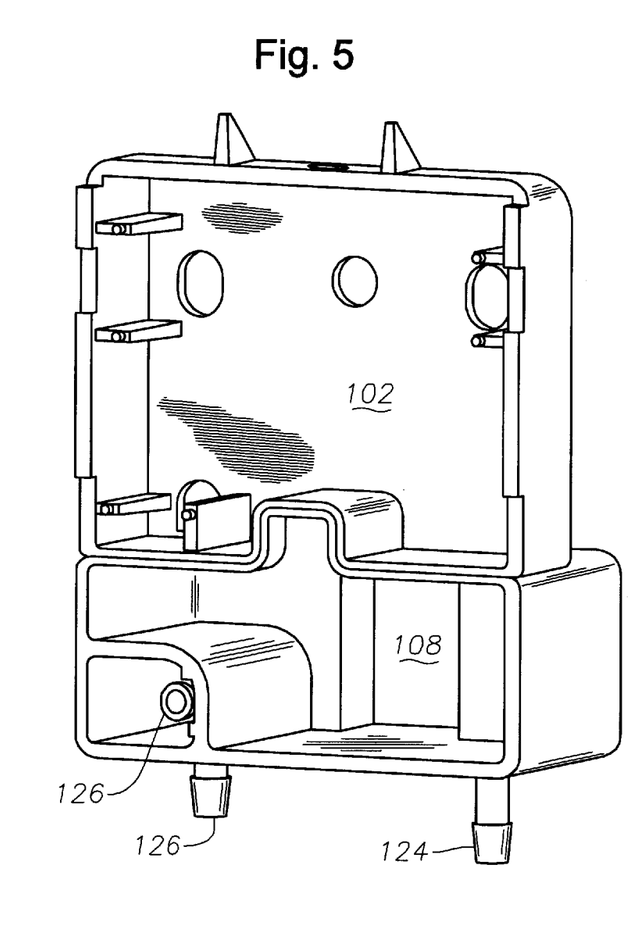
FIG. 5 is a front, perspective view of the body of the cassette of FIG. 3.
Figure 6:
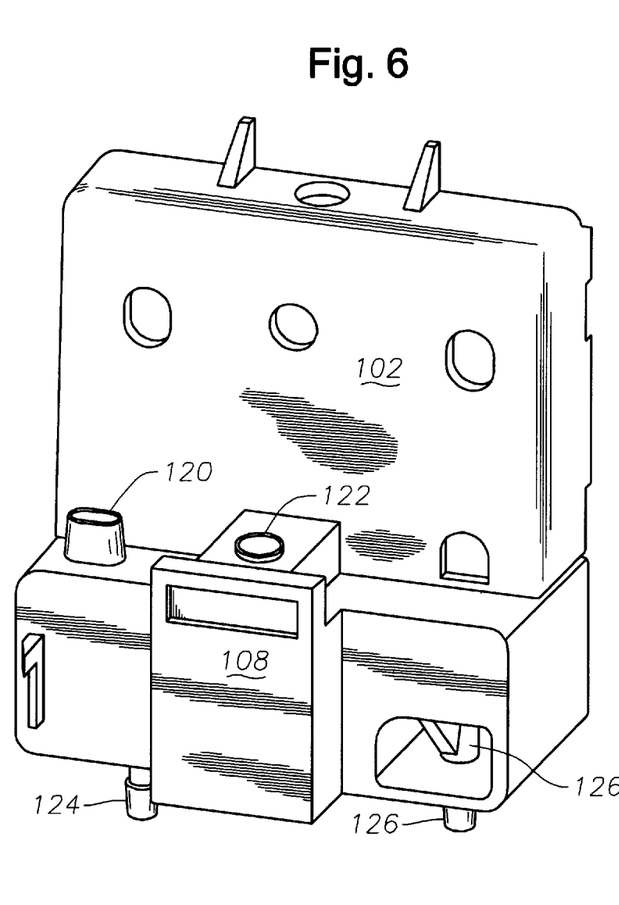
FIG. 6 is a rear, perspective view of the body of the cassette of FIG. 3.
Figure 7:
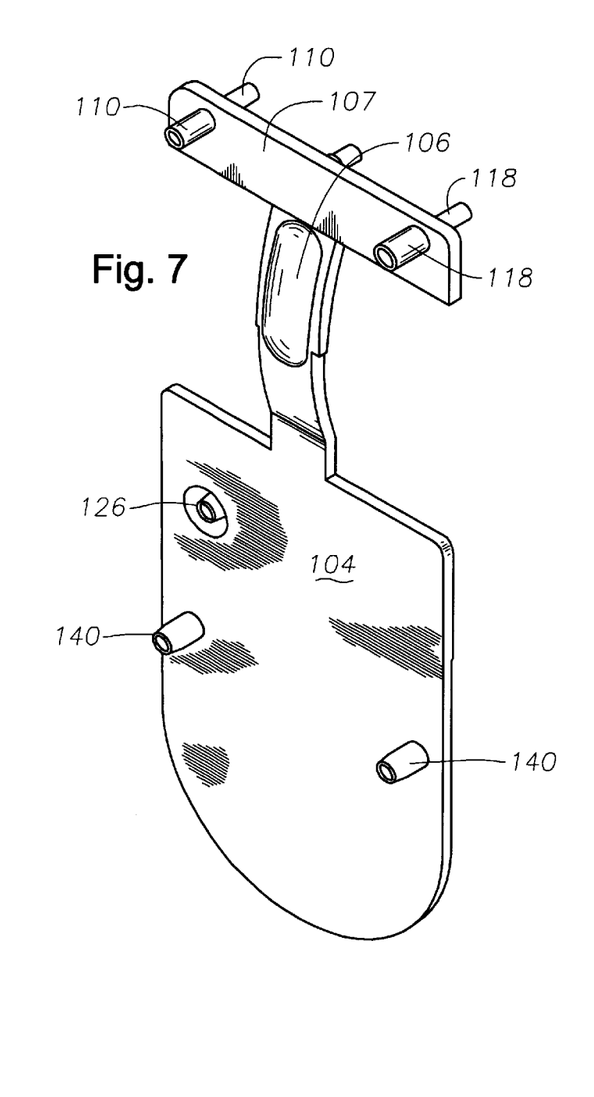
FIG. 7 is a front, perspective view of the cover of the cassette of FIG. 3.

Irrigation inlet 110 is for fluidly coupling to a source of a conventional ophthalmic infusion fluid (not shown), such as saline solution or BSS PLUS® intraocular irrigating solution, via conventional medical grade flexible tubing. By way of example, the source of infusion fluid is preferably a bottle disposed above cassette 100 via a conventional IV pole.

Figure 8:
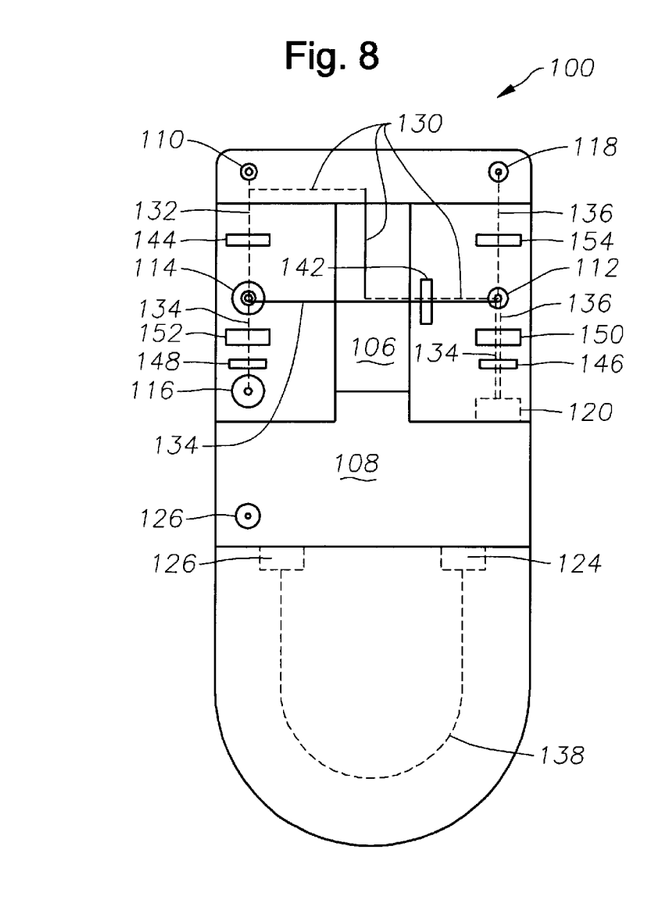
FIG. 8 is a front schematic view of the fluidics of the cassette of FIG. 3.

Referring specifically to FIG. 8, the preferred routings of the various manifolds that define the fluidics of cassette 100 are schematically illustrated. Portions of a manifold on the front side of cassette 100 are designated with solid lines, and portions of a manifold on the rear side of cassette 100 are designated with dashed lines. All of the manifolds of cassette 100 are preferably made from medical grade silicone or other conventional, flexible plastic. More specifically, a manifold 130 fluidly couples irrigation inlet 110 and anterior irrigation outlet 112. A manifold 132 fluidly couples irrigation inlet 110 and posterior irrigation outlet 114. Manifolds 130 and 132 are preferably formed as an integral component. A manifold 134 fluidly couples general aspiration port 116 and first vacuum chamber port 120. A manifold 136 fluidly couples posterior aspiration port 118 and first vacuum chamber port 120. Manifolds 134 and 136 are preferably formed as an integral component. A conventional vacuum source is preferably fluidly coupled to second vacuum chamber port 122 via a console connection (not shown). This console connection is described in greater detail in U.S. Pat. No. 5,676,530, which is incorporated herein in its entirety by this reference. The conventional vacuum source is preferably part of a conventional ophthalmic surgical system capable of performing a combined procedure, such as the Accurus® 800 CS surgical system. A manifold 138 fluidly couples third vacuum chamber port 124 with drainage bag port 126. Drainage bag port 126 is for fluidly coupling with a conventional drain bag (not shown) supported by flanges 140.

Cassette 100 is for removably disposing in a conventional cassette receiving mechanism of a conventional ophthalmic surgical system such as the Accurus® 800 CS surgical system. The cassette receiving mechanism of the Accurus® surgical system is described in more detail in U.S. Pat. Nos. 5,676,530 and 5,588,815, which are incorporated herein in their entirety by this reference. When cassette 100 is disposed in the cassette receiving mechanism, second vacuum chamber port 122 is preferably fluidly coupled with a conventional source of vacuum within the surgical system. In addition, various portions of the manifolds located on the rear side of cassette 100 are positioned for operative engagement with various occluder valves and microreflux valves located in the surgical system. Each of these valves is preferably a conventional plunger valve that can be actuated to "pinch off" and close the manifolds in response to an electrical signal generated by the surgical system. The microreflux valves preferably have a slightly larger footprint than the occluder valves. More specifically, as shown in FIG. 8, manifold 130 is positioned for operative engagement with an occluder valve 142. Manifold 132 is positioned for operative engagement with an occluder valve 144. Manifold 134 is positioned for operative engagement with occluder valves 146 and 148, and microreflux valves 150 and 152. Manifold 136 is positioned for operative engagement with occluder valves 146,and 154, and microreflux valve 150. Furthermore, manifold 138 is positioned for operative engagement with a conventional peristaltic pump (not shown) disposed in the surgical system. Peristaltic pump opens and closes manifold 138 in order to pump aspirated ophthalmic tissue and fluid from vacuum chamber 108, through third vacuum chamber port 124, into manifold 138, through drainage bag port 126, and into the drain bag.

Having described the structure of the preferred embodiment of cassette 100, the preferred method of using cassette 100 in a combined anterior segment and posterior segment ophthalmic surgical procedure in conjunction with a conventional ophthalmic surgical system will now be described in greater detail with reference to FIGS. 3 through 9. Cassette 100 is disposed in the cassette receiving mechanism of the conventional surgical system. A conventional source 160 of ophthalmic infusion fluid 30 is fluidly coupled to irrigation inlet 110 via tubing 162. The source of ophthalmic fluid may be, by way of example, bottle 28 described hereinabove in connection with FIGS. 1 and 2. In addition, although not shown in FIG. 9, a tube providing pressurized air may be fluidly coupled to tubing 162 so as to provide different infusion pressures for fluid 30 without the necessity of moving source 160 to different heights above cassette 100. One method of providing such different infusion pressures is to use a vented gas forced irrigation/infusion tubing set available from Alcon Laboratories, Inc. as tubing 162. A conventional drain bag is attached to cassette 100 via flanges 140. The bag is fluidly coupled to drainage bag port 126 in the conventional manner. A conventional ultrasonic handpiece 164 is fluidly coupled to cassette 100. Ultrasonic handpiece 164 is preferably a phacoemulsification handpiece. More specifically, anterior irrigation outlet 112 of cassette 100 is fluidly coupled to irrigation inlet 166 of handpiece 164 via tubing 168. In addition, aspiration port 170 of handpiece 164 is fluidly coupled to general aspiration port 116 of cassette 100 via tubing 172. A conventional vitrectomy probe 174 is fluidly coupled to cassette 100. Probe 174 may be pneumatically or electrically driven, and probe 174 may be a "guillotine style" or a "rotational style" vitrectomy probe. More specifically, aspiration port 176 of probe 174 is fluidly coupled to posterior aspiration port 118 of cassette 100 via tubing 178. A conventional infusion cannula 180 is fluidly coupled to cassette 100. More specifically, port 182 of cannula 180 is fluidly coupled to posterior irrigation outlet 114 of cassette 100 via tubing 184. Tubing 168, 172, 178, and 184 are preferably conventional medical grade flexible tubing. Although not shown in FIG. 9, ultrasonic handpiece 164 may be replaced with a conventional irrigation handpiece or a conventional irrigation/aspiration handpiece for certain anterior segment procedures.

Figure 9:
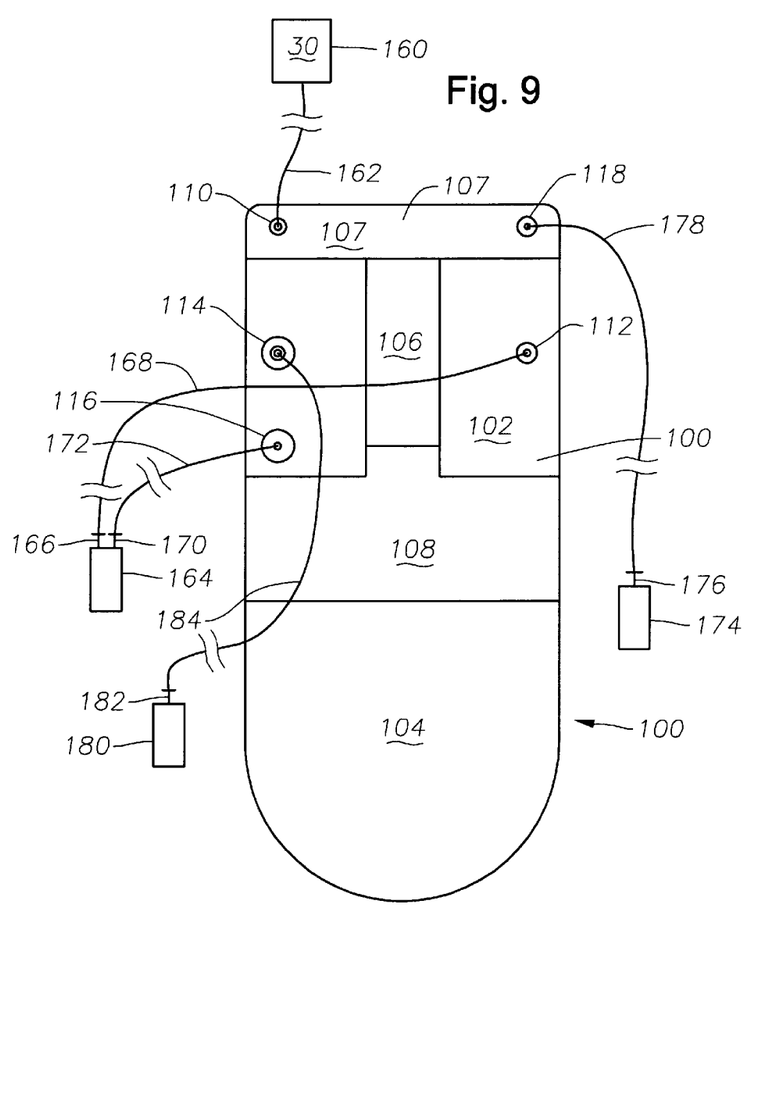
FIG. 9 is a front schematic view of the cassette of FIG. 3 being used in a combined ophthalmic surgical procedure according to a preferred method of the present invention.

The surgeon typically then performs the anterior segment portion of the combined procedure using ultrasonic handpiece 164. More specifically, the surgeon selects an anterior segment mode on the conventional surgical system. The anterior segment mode is utilized to control ultrasonic handpiece 164. In the anterior segment mode, the surgical system actuates occluder valve 142 to open manifold 130, allowing infusion fluid to flow from irrigation inlet 110 to anterior irrigation outlet 112. During the procedure, occluder valve 142 may be actuated via the surgical system to start or stop this flow of irrigation fluid as desired. The surgical system also actuates occluder valve 144 to close manifold 132, preventing the flow of infusion fluid from irrigation inlet 110 to posterior irrigation outlet 114. The surgical system also actuates occluder valves 146 and 148 to open manifold 134, providing vacuum to general aspiration port 116. The surgical system further actuates occluder valve 154 to close manifold 136, stopping vacuum to posterior aspiration port 118. Ultrasonic handpiece 164 may then be utilized to perform the anterior segment portion of the combined procedure. During the procedure, cassette 100 provides infusion fluid 30 to infusion inlet 166 of handpiece 164 via anterior irrigation outlet 112 and tubing 168 to cool the tip of handpiece 164 at the intraocular incision and to replace aspirated fluid and tissue. Cassette 100 also provides vacuum to aspiration port 170 of handpiece 164 via general aspiration port 116 and tubing 172. Such vacuum removes ophthalmic tissue and fluid aspirated by handpiece 164 into vacuum chamber 108 via tubing 172 and manifold 134.

During the anterior segment portion of the combined procedure, a surgeon may need to perform a microreflux operation if, by way of example, portions of the posterior capsule or iris become too close to the cutting tip of ultrasonic handpiece 164. The microreflux operation causes a small pressure wave or impulse to be sent from cassette 100 to aspiration port 170 of ultrasonic handpiece 164 by displacement of a small bolus of fluid within the manifolds of cassette 100. This pressure wave exits the tip of ultrasonic handpiece 164 and moves the posterior capsule or iris away from the tip of handpiece 164. More specifically, occluder valve 154 has already been actuated to close manifold 136, and occluder valve 148 has already been actutated to open manifold 134, at the beginning of the anterior segment mode. The surgical system actuates occluder valve 146 to close manifold 134. The surgical system then actuates microreflux valve 150 to momentarily close manifold 134, displacing fluid and creating a pressure wave that will exit through port 116. Once the advancing pressure wave passes microreflux valve 152, the surgical system preferably actuates microreflux valve 152 to close manifold 134, augmenting the pressure wave. The pressure wave exits port 116 and travels through tubing 172 and aspiration port 170 of handpiece 164 and out through the tip of the handpiece. The surgical system then closes occluder valve 148 and opens occluder valve 146, before opening microreflux valves 150 and 152, to prevent microaspiration. If timed correctly, this closing of occluder valve 148 may also augment the microreflux pressure wave. The surgical system reopens occluder valve 148 to continue normal anterior segment aspiration.

The surgeon then typically performs the posterior segment portion of the combined procedure using vitrectomy probe 174 and infusion cannula 180. More specifically, the surgeon selects a posterior segment mode on the conventional surgical system. The posterior segment mode is used to control probe 174 and cannula 180. In the posterior segment mode, the surgical system actuates occluder valve 144 to open manifold 132, allowing infusion fluid to flow from irrigation inlet 110 to posterior irrigation outlet 114. During the procedure, occluder valve 144 may be actuated via the surgical system to start or stop this flow of irrigation fluid as desired. The surgical system also actuates occluder valve 142 to close manifold 130, preventing the flow of infusion fluid from irrigation inlet 110 to anterior irrigation outlet 112. The surgical system also actuates occluder valves 146 and 154 to open manifold 136, providing vacuum to posterior aspiration port 118. The surgical system further actuates occluder valve 152 to close manifold 134, stopping vacuum to general aspiration port 116. Vitrectomy probe 174 and infusion cannula 180 may then be utilized to perform the posterior segment portion of the combined procedure. During the procedure, cassette 100 provides infusion fluid 30 to port 182 of cannula 180 via posterior irrigation outlet 114 and tubing 184 to maintain appropriate intraocular pressure of the eye. Cassette 100 also provides vacuum to aspiration port 176 of probe 174 via posterior aspiration port 118 and tubing 178. Such vacuum removes ophthalmic tissue and fluid aspirated by probe 174 into vacuum chamber 108 via tubing 178 and manifold 136.

During the posterior segment portion of the combined procedure, a surgeon may need to perform a microreflux operation if, by way of example, portions of the retina become too close to the cutting port vitrectomy probe 174. The microreflux operation causes a small pressure wave or impulse to be sent from cassette 100 to aspiration port 176 of vitrectomy probe 174, by displacement of a small bolus of fluid within the manifolds of cassette 100. This pressure wave exits the cutting port of probe 174, and moves the retina away from the cutting port of probe 174. More specifically, occluder valve 148 has already been actuated to close manifold 134, and occluder valve 154 has already been actuated to open manifold 136, and the beginning of posterior segment mode. The surgical system actuates occluder valve 146 to close manifold 136. The surgical system then actuates microreflux valve 150 to momentarily close manifold 136, displacing fluid and creating a pressure wave that exits through port 118. This pressure wave travels through tubing 178 and aspiration port 176 of probe 170 and out through the cutting port of the probe. The surgical system then closes occluder valve 154 and opens occluder valve 146, before opening microreflux valve 150, to prevent microaspiration. If timed correctly, this closing of occluder valve 154 may augment the microreflux pressure wave. The surgical system reopens occluder valve 154 to continue normal posterior segment aspiration.

In both the anterior segment portion and the posterior segment portion of the combined procedure, aspirated ophthalmic tissue and fluid is removed from vacuum chamber 108 into a drain bag via third vacuum chamber port 124, manifold 138, and drainage bag port 126. This aspirated fluid is removed via the operative engagement of a peristaltic pump with manifold 138 as described hereinabove.

Figure 10:
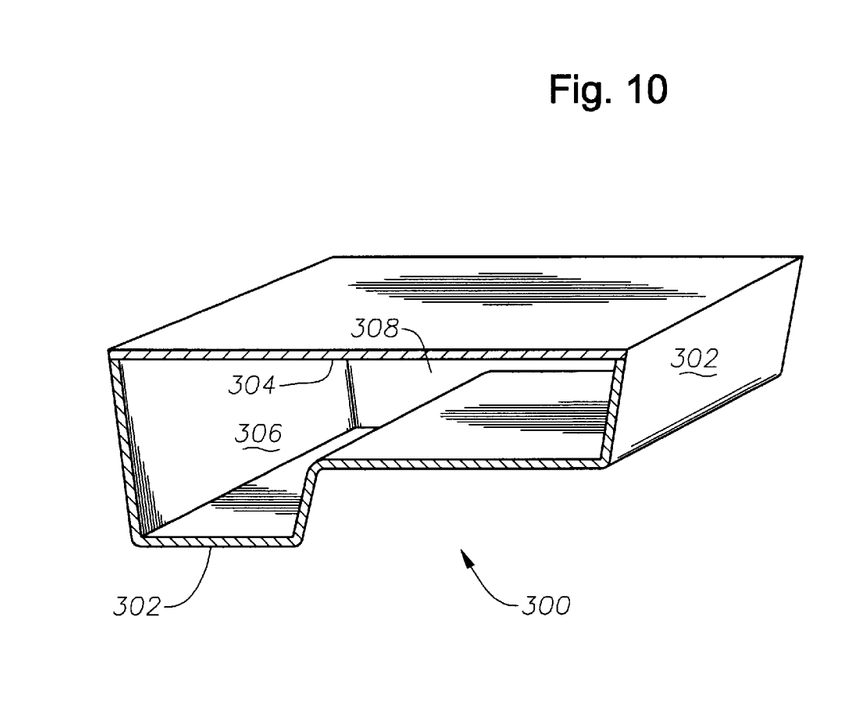
FIG. 10 is a perspective, partially sectional view of a package for the cassette of the present invention and its associated consumables.

FIG. 10 illustrates an exemplary package 300 for housing cassette 100 and its associated consumables for distribution purposes. Package 300 generally includes a body 302 and a cover 304. Body 302 has an interior 306 and an opening 308. Body 302 is preferably formed from conventional plastics in a shape to conveniently store cassette 100 and its associated consumables. Cover 304 is removably coupled to body 302 and is disposed over opening 308. Cover 304 is preferably formed from a breathable, porous material, such as, by way of example, high density polyethylene. A preferred material for cover 304 is Tyvek® available from E. I. duPont de Nemours and Company of Wilmington, Del. Cover 304 is preferably removably coupled to body 302 via an adhesive.

Package 300 is preferably suitable for sterilization via conventional gamma radiation or ethylene oxide processes.

It will be apparent to those skilled in the art that the surgical system may actuate the occluder valves of cassette 100 to provide irrigation from anterior irrigation outlet 112 and posterior irrigation outlet 114 simultaneously, or to prevent irrigation from both irrigation outlet 112 and posterior irrigation outlet 114, if desired. Similarly, the surgical system may actuate the occluder valves of cassette 100 to provide for vacuum from general aspiration port 116 and posterior aspiration port 118 simultaneously, or to prevent vacuum to both general aspiration port 116 and posterior aspiration port 118, if desired.

From the above, it may be appreciated that the present invention provides a surgeon with a simplified method of performing a combined anterior segment and posterior segment ophthalmic surgical procedure. Significantly, using the present invention, the surgeon no longer must changeover the surgical system from anterior segment consumables to posterior segment consumables in order to complete the combined procedure.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic surgical cassette for removably disposing in a cassette receiving mechanism of an ophthalmic surgical system, said system comprising a source of vacuum and first and second plunger valves, said cassette comprising:

a body having a rear surface;

a vacuum chamber disposed within said body for fluidly coupling to said source of vacuum;

an aspiration port disposed on said body for providing vacuum to a first ophthalmic microsurgical instrument; and a flexible aspiration manifold fluidly coupled to said aspiration port and said vacuum chamber and at least partially disposed proximate said rear surface so as to allow operative engagement with said first and second plunger valves;

whereby during operation of said ophthalmic surgical system, actuation of said first plunger valve pinches said aspiration manifold between said first plunger valve and said rear surface to create a microreflux pressure wave within said aspiration manifold that eventually exits said aspiration port, and actuation of said second plunger valve pinches said aspiration manifold between said second plunger valve and said rear surface to augment said microreflux pressure wave.

* * * * *

UNITED STATES PATENT AND TRADEMARK OFFICE
CERTIFICATE OF CORRECTION

PATENT NO. : 6,824,525 B2
DATED : November 30, 2004
INVENTOR(S) : Nader Nazarifar It is certified that error appears in the above-identified patent and that said Letters Patent is hereby corrected as shown below:

Title page,
Item [75], Inventors, delete "; Dennis L. Steppe, Corona, CA (US)".

Signed and Sealed this

Twenty-second Day of March, 2005

JON W. DUDAS
*Director of the United States Patent and Trademark Office*